(12) United States Patent
Prado

(10) Patent No.: US 9,575,019 B2
(45) Date of Patent: Feb. 21, 2017

(54) DETECTING HAZARDOUS MATERIALS IN CONTAINERS UTILIZING NUCLEAR MAGNETIC RESONANCE BASED MEASUREMENTS

(76) Inventor: Pablo J. Prado, San Diego, CA (US)

(*) Notice: Subject to any disclaimer, the term of this patent is extended or adjusted under 35 U.S.C. 154(b) by 507 days.

(21) Appl. No.: 14/345,917

(22) PCT Filed: Sep. 2, 2012

(86) PCT No.: PCT/US2012/053575
§ 371 (c)(1),
(2), (4) Date: Mar. 19, 2014

(87) PCT Pub. No.: WO2013/077922
PCT Pub. Date: May 30, 2013

(65) Prior Publication Data
US 2014/0225614 A1    Aug. 14, 2014

Related U.S. Application Data

(60) Provisional application No. 61/627,115, filed on Sep. 19, 2011.

(51) Int. Cl.
*G01V 3/00* (2006.01)
*G01N 24/08* (2006.01)
(Continued)

(52) U.S. Cl.
CPC ........... *G01N 24/084* (2013.01); *G01R 33/448* (2013.01); *G01R 33/4616* (2013.01)

(58) Field of Classification Search
USPC ....................................................... 324/309
See application file for complete search history.

(56) References Cited

U.S. PATENT DOCUMENTS 5,500,591 A    3/1996    Smith et al.
5,698,979 A    12/1997    Taicher et al.
(Continued)

OTHER PUBLICATIONS

International Search Report and written opinion dated May 13, 2013, issued for International Application No. PCT/US2012/053575.

(Continued)

*Primary Examiner* — Rodney Fuller
(74) *Attorney, Agent, or Firm* — Procopio, Cory, Hargreaves & Savitch LLP; Pattric J. Rawlins

(57) ABSTRACT

A method of detecting hazardous materials in containers utilizing nuclear magnetic resonance (NMR) technology. The presence of precursors (e.g., $H_2O_2$) and/or nitrogen in the liquid in the container is determined by placing the container in a static magnetic field, exciting the container with electromagnetic pulses having a frequency corresponding to proton NMR and 14N NMR, and receiving radio frequency (RF) signals through a probe. The excitation pulses are configured to enable detection of the presence of precursors and nitrogen in the container, and may comprise a sequence of short RF pulses. The presence of nitrogen and/or explosive precursors is determined by detecting and evaluating NMR measurement signal amplitudes and relaxation times from the received RF signals. An apparatus comprising a magnet that generates a magnetic field and a probe that generates RF pulses and receives NMR measurement signals from the sampled container in accordance with the aforementioned method.

14 Claims, 12 Drawing Sheets

(51) Int. Cl.
*G01R 33/44* (2006.01)
*G01R 33/46* (2006.01)

(56) References Cited

U.S. PATENT DOCUMENTS

| | | | |
|---|---|---|---|
| 6,392,408 B1 | 5/2002 | Barrall et al. | |
| 7,355,402 B1 | 4/2008 | Taicher et al. | |
| 7,511,496 B2* | 3/2009 | Schiano | G01R 33/34053 324/307 |
| 7,759,938 B2 | 7/2010 | Prado et al. | |
| 2004/0140800 A1 | 7/2004 | Madio et al. | |
| 2005/0202570 A1* | 9/2005 | Pusiol | G01R 33/441 436/173 |
| 2008/0309339 A1* | 12/2008 | Chisholm | G01N 24/087 324/315 |
| 2010/0090698 A1 | 4/2010 | Blumich et al. | |
| 2011/0019797 A1* | 1/2011 | Morton | G01N 23/046 378/57 |
| 2015/0077102 A1* | 3/2015 | Mandal | G01N 24/084 324/303 |
| 2016/0077178 A1* | 3/2016 | Song | G01R 33/441 324/309 |

OTHER PUBLICATIONS

State Intellectual Property Office, Office Action (with English translation) issued in corresponding CN Application No. 2012800477236, dated Jan. 26, 2016, 14 pages.
Extended European Search Report received in European patent application No. 12851906.3 and dated Mar. 24, 2015, 10 pages.
Burnett et al. "Signal processing considerations in NMR detection of liquid explosives," Proceedings of SPIE, vol. 1824, Nov. 16, 1992, 11 pages.
Espy et al. "Progress on Detection of Liquid Explosives Using Ultra-Low Field MRI," IEEE Transactions on Applied Superconductivity, vol. 21, No. 3, Jun. 1, 2011, 4 pages.
Gradisek et al. "NMR-Based Liquid Explosives Detector," Applied Magnetic Resonance, vol. 38, No. 4, Jun. 18, 2010, 9 pages.
Gudmundson et al. "Detection and Classification of Liquid Explosives Using NMR," Acoustics, Speech and Signal Processing, Apr. 19, 2009, 4 pages.
King et al. "Development and evaluation of magnetic resonance technologies, particularly NMR, for detection of explosives," Applied Magnetic Resonance, vol. 25, No. 3-4, Sep. 1, 2004, 31 pages.
Kumar, "Liquid-contents verification for explosives, other hazards, and contraband by magnetic resonance," Applied Magnetic Resonance, vol. 25, No. 3-4, Sep. 1, 2004, 13 pages.
Kumar et al. "Screening sealed bottles for liquid explosives," Proceedings of SPIE, vol. 2934, Jan. 29, 1997, 12 pages.
Kumar et al. "Magnetic-resonance-based system for chemical agent screening," Proceedings of SPIE, vol. 5071, Sep. 23, 2003, 12 pages.
Mauler et al. "Identification of Liquids Encountered in Carry-on-Luggage by Mobile NMR," Explosives Detection Using Magnetic and Nuclear Resonance Techniques, 2009, 13 pages.

* cited by examiner

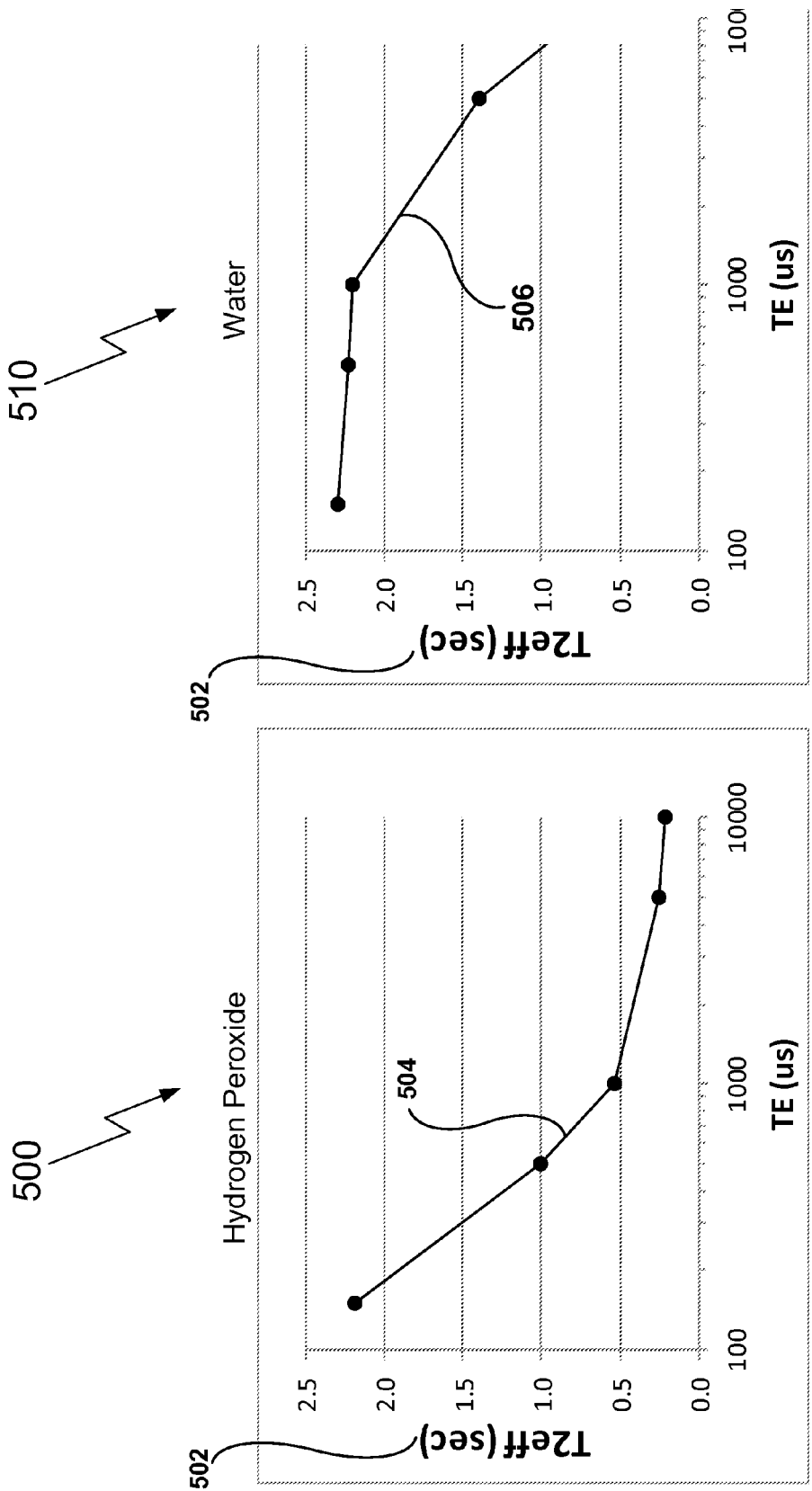

DETECTING HAZARDOUS MATERIALS IN CONTAINERS UTILIZING NUCLEAR MAGNETIC RESONANCE BASED MEASUREMENTS

RELATED APPLICATION(S)

This application claims priority of U.S. Provisional Patent Application Ser. No. 61/627,115, filed on Sep. 19, 2011, entitled "APPARATUS AND METHOD TO DETECT HAZARDOUS MATERIALS IN BOTTLES AND OTHER CONTAINERS," which application is incorporated in its entirety in this application by this reference.

BACKGROUND OF THE INVENTION

1. Field of the Invention

The invention is related generally to nuclear magnetic resonance (NMR) technology, and more particularly, to methods utilizing NMR to non-invasively inspect unopened containers to screen for liquid explosives and explosive precursors.

2. Related Art

During the past decades, there has been an increased threat of terrorist attacks involving explosives, including Improvised Explosive Devices (IEDs). Because of this increased threat, security concerns are now greater and extend to airports, seaports, rail stations, prisons, embassies, and many other secured and unsecured facilities.

One of the oldest known explosives is gunpowder, a solid explosive made up of potassium nitrate, charcoal, and sulfur. However, liquid explosives can also be manufactured from common chemicals that may be used for legitimate purposes and thus are legally obtainable and readily available. Improvised explosives can be mixtures of an oxidizer, which supplies oxygen to a chemical reaction, and a fuel, which supplies the element that reacts explosively with the oxygen.

Even though explosives in liquid form are highly sensitive to shocks, they may be transported in sealed containers by preparing solutions that keep the compound more stable or by transporting the components needed to form an explosive in separate containers. In general, liquid explosives are chemically easier to combine and simpler to ignite than solid explosives.

Several nitrogen-containing and peroxide-based compounds are used to create homemade explosives, and generally, liquid explosives can be classified as containing either peroxide compounds or the element nitrogen. Hydrogen peroxide is of particular interest for security checkpoints as it may be used as an explosive precursor. Contact between hydrogen peroxide and combustible materials such as wood, paper, or oil, causes spontaneous ignition or combustion. When mixed with materials such as sugars, alcohols, or acetone, the result is a powerful explosive. Hydrogen peroxide chemically resembles water, so it is a good candidate for a smuggled explosive precursor.

Vapor and trace detectors may be used to screen containers for explosives, but these require direct contact with the compounds inside the containers. In addition, emulsion and slurry-based compounds such as ammonium nitrate have low vapor pressure, making them more difficult to detect with vapor and trace detectors. Optical detection technologies such as Raman and infrared spectroscopy have been demonstrated to be effective for detecting some hazardous liquids, but require illumination of the sample and thus are limited by the opacity of the container's walls.

Nuclear magnetic resonance (NMR) has been demonstrated to be an effective method of discriminating between the expected parameters of a known liquid and an altered liquid in an unopened container, that is, ensuring that the liquid specified on the bottle label matches the bottle content. This method, however, is based on content verification, which requires an extensive knowledge base of the NMR responses for all compounds of interest. Hence, the implementation of such a method is not practical as the knowledge database is extremely extensive and constantly changing.

Accordingly, a need exists for a method of detecting those elements always found in liquid explosives quickly, efficiently, and inexpensively, with a high degree of accuracy and a low incidence of false alarms.

SUMMARY

In view of the above, a method of detecting the presence of explosive precursors (e.g., hydrogen peroxide ($H_2O_2$)) and nitrogen (N) in unopened, non-metallic containers, without opening same, utilizing nuclear magnetic resonance (NMR) technology is provided. The presence of precursors and/or N in the liquid in the container is determined by placing the container in a static magnetic field, exciting certain NMR-active nuclei (hydrogen or $^1H$, and $^{14}N$) in the liquid with electromagnetic pulses having frequencies corresponding to proton NMR (or hydrogen, $^1H$ NMR) and $^{14}N$ NMR, and receiving free induction decay (FID) signals (i.e., RF signals (NMR measurement signals) based on the responsive FID) through a radio frequency (RF) probe. The excitation pulses are configured to enable the detection of the presence of explosive precursors, e.g. hydrogen peroxide, and nitrogen (i.e., nitrogen or nitrogen-inclusive compounds) in the liquid in the container, and comprise a sequence of short RF pulses. A common pulse sequence used is the Carr-Purcell-Meiboom-Gill (CPMG) sequence. The presence of the precursors and nitrogen is determined by detecting and evaluating NMR measurement signal amplitudes and relaxation times, where the relaxation times comprise spin-spin relaxation times ($T_2$), spin-lattice relaxation times ($T_1$), and functions of inter-echo times ($T_E$), such as effective multi-pulse sequence signal decay time ($T_{2eff}$), e.g., during a CPMG-type pulse sequence.

An apparatus (or system) comprising a permanent magnet or electro-magnet generating a static magnetic ($B_o$) field in or on which the container may be placed and a probe comprising a single coil or a plurality of coils that generate RF pulses and receive decay signals from the sampled container in accordance with the aforementioned method is also disclosed. Alternatively, a superconducting magnet may be utilized for generating the static magnetic field. The pulse transmission and signal receive elements may be the same or separate probes. As appreciated by persons skilled in the art, the apparatus may include hardware (e.g., an electronics-based processor) and/or software as needed for processing the signals to detect and evaluate NMR signal amplitudes and relaxation times, as well as perform any other determinations and calculations described herein for detecting explosive precursors and/or nitrogen. It is to be understood that the features mentioned above and those yet to be explained below may be used not only in the respective combinations indicated herein but also in other combinations or in isolation without departing from the scope of the invention.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figure(s). The components in the figures are not necessarily to scale, emphasis instead being placed upon illustrating the principles of the invention. In the figures, like reference numerals designate corresponding parts throughout the different views.

FIG. 5A shows a graph illustrating effective signal decay time ($T_{2eff}$) for a CPMG pulse sequence with varying echo times (TE) for pharmacy-grade hydrogen peroxide ($H_2O_2$).

FIG. 5B shows a graph illustrating $T_{2eff}$ for a CPMG pulse sequence with varying TEs for water ($H_2O$).

DETAILED DESCRIPTION

Figure 1A:
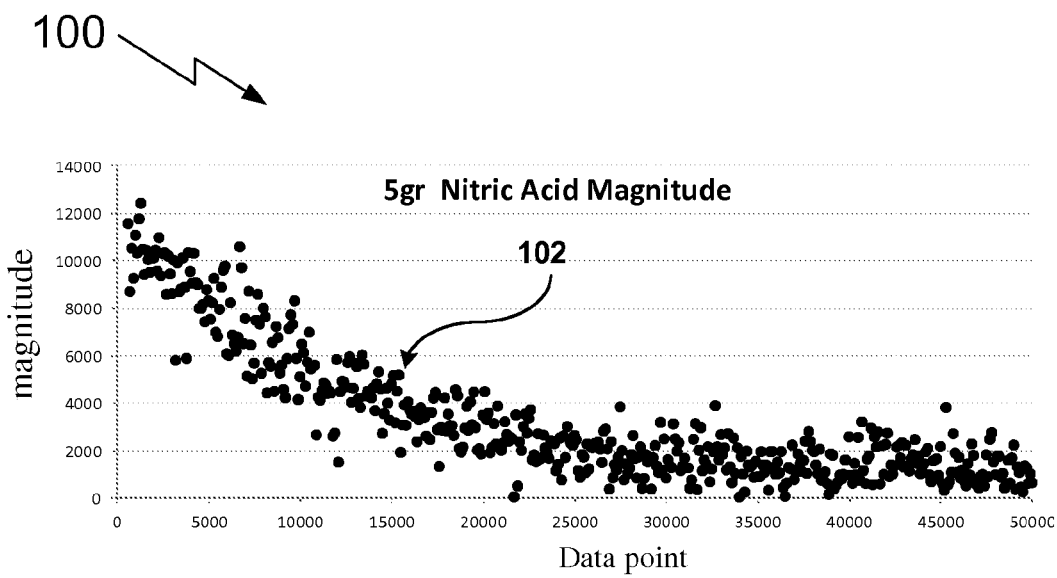
FIG. 1A shows a graph of a time series of nitric acid $^{14}$N nuclear magnetic resonance (NMR) signal decay with rapid accumulation of 32 scans using a Carr-Purcell-Meiboom-Gill (CPMG) pulse sequence.

It is to be understood that the following description of various implementations is given only for the purpose of illustration and is not to be taken in a limiting sense. The partitioning of in the function blocks, modules or units shown in the drawings is not to be construed as indicating that these function blocks, modules or units are necessarily implemented as physically separate units. Functional blocks, modules or units shown or described may be implemented as separate units, circuits, chips, functions, modules, or circuit elements. One or more functional blocks or units may also be implemented in a common circuit, chip, circuit element or unit.

A method of detecting hazardous materials is disclosed. The hazardous materials may, for example, be of the type utilized as liquid explosives, or as components or precursors of liquid explosives. The method of detecting hazardous materials combines inspection schemes to determine the presence of the element nitrogen and explosive precursors (such as hydrogen peroxide) in unopened containers using NMR. The nitrogen is detected using $^{14}$N NMR and the precursors are detected using $^1$H proton NMR as described in more detail below.

Non-hazardous substances carried by airplane passengers, personnel entering secured facilities, such as courtrooms, prisons, and the like, generally contain no nitrogen, or the amounts of nitrogen are significantly smaller than those of nitrogen-containing hazardous materials, such those shown in the Table 1 below. There are no significant amounts of nitrogen in water, perfumes, club soda, rum, gin, vodka, sport drinks, or caffeine-free teas. Only trace amounts of nitrogen are found in whiskey, tequila, apple juice, coffee, and some teas. Low amounts of nitrogen may be found in some skin-care products. Nitrogen is present by less than 0.1% in wine, beer, and orange juice. Therefore, a high concentration of nitrogen in a liquid is an indication of a hazardous material.

TABLE 1

Examples of Hazardous Materials

| Material | Formula |
| --- | --- |
| Peroxide-Based Explosive Precursors | |
| Hydrogen Peroxide | $H_2O_2$ |
| Hydrogen Peroxide Mixtures: adding materials such as coffee, sugar, and sugary orange juice powders | $H_2O_2$ and additive |
| Methyl Ethyl Ketone Peroxide | $C_4H_{10}O_4$ |
| Nitrogen-Containing Explosives | |
| Ammonium Nitrate in Solution | (NH4)(NO3) |
| Ethylene Glycol Dinitrate, Nitroglycol | $C_2H_4N_2O_6$ |
| Hydrazine | $N_2H_4$ |
| Nitric Acid | $HNO_3$ |
| Nitrobenzene | $C_6H_5NO_2$ |
| Nitroethane | $C_2H_5NO_2$ |
| Nitroglycerin | $C_3H_5N_3O_9$ |
| Nitroglycol | $C_2H_4N_2O_6$ |
| Nitromethane | $CH_3NO_2$ |
| Picatinny Liquid Explosive | $CH_3NO_2, C_2H_8N_2$ |
| Propylene Glycol Dinitrate | $C_3H_6N_2O_6$ |
| Tetranitromethane | $CN_4O_8$ |

In conventional MR, a scanned sample is placed in a uniform, temporally constant magnetic field. The magnetic field causes nuclear spins within nuclei of elements of the sample to effectively line up parallel to the magnetic field direction. This orientation is permuted by exciting these nuclei with one or a series of radio-frequency (RF) pulses where the frequency of the RF pulses are dependent upon the strength of the magnetic field and the nuclei under observation. As these excited nuclei realign to the external magnetic field, they emit an RF signal that induces a voltage in a receiver probe. The characteristics of the signals that the nuclei emit depend on the composition of the nucleus, its chemical surroundings, and on the strength of the external magnetic field.

Nitrogen-Containing Liquids $^{14}N$ is one of two stable (non-radioactive) isotopes of the chemical element nitrogen and makes up approximately 99.63% of natural nitrogen. $^{14}N$ is quadrupolar, with nuclear spin I=1, which results in NMR line broadening and an associated fast signal decay. The broadening is moderate because the quadrupole coupling is low, $Q=0.017 \times 10^{-28}$ $m^2$. The NMR resonance frequency for nitrogen is 7.2% that of hydrogen. $^{14}N$ presents a lower NMR sensitivity than $^1H$, even with its high natural abundance of 99.63%. Therefore, sensitivity enhancement techniques may be used with the embodiments. For example, the base sensitivity may be increased by 1) adding echoes in a multi-echo pulse sequence, 2) integrating the filtered signal (for example, using a match, Hanning, or box filter) over each echo or Fourier Transformed signal, 3) performing signal averaging by repeating and adding scans, 4) using cross-polarization methods and receiving NMR measurement signals at nitrogen or proton frequencies, and 5) using steady-state pulse sequences resulting in noise reduction by data accumulation. Data accumulation (or averaging) improves the signal-to-noise ratio by a square root of the scanning time. Cross-polarization methods may also be used in combination with the enhancements steps 1) to 3).

Figure 11:
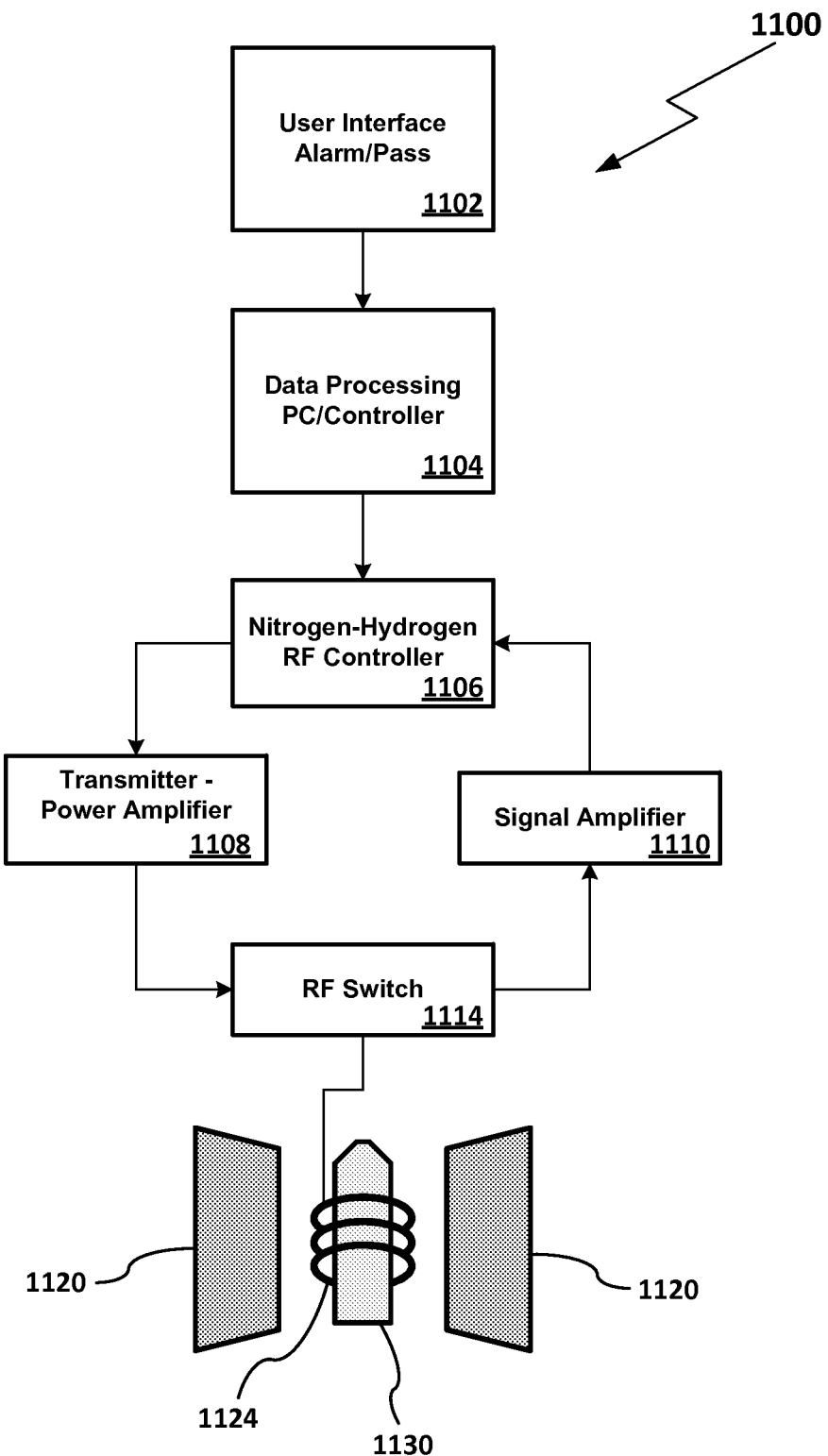
FIG. 11 shows a block diagram of an example of an apparatus configured to detect liquid explosives in an unopened container in accordance with the invention.

As examples of effective nitrogen-containing hazardous liquid detection, $^{14}N$ NMR signals were generated from nitric acid ($HNO_3$, which forms explosive mixtures with nitrobenzene or picric acid), and nitromethane using a 2.4 Tesla magnet. The $^{14}N$ resonance frequency at the measured field is 7.153 MHz. FIG. 11, described below, is schematically representative of an NMR apparatus or system (e.g., a "bottle scanner") that may be utilized for implementing the methods disclosed herein.

FIG. 1A shows a graph 100 of the time series 102 of nitric acid $^{14}N$ NMR signals with rapid accumulation of 32 scans using a Carr-Purcell-Meiboom-Gill (CPMG) pulse sequence. The sample's filling factor for this test was below 25%. Signal accumulation during a total of 1 second was achieved with repetition times of 30 ms, which was near optimal for the short spin-lattice relaxation of the sample, $T_1=20+/-5$ ms. The acquisition window is 100 ms, with a dwell time of 100 μs, and 1024 acquisition points. Applying the signal-to-noise ratio (SNR) improvement steps 1) to 3) described above and estimating the sensitivity at lower static fields of 0.25 T result in SNR=6 in a 1 sec acquisition for nitric acid. This SNR level indicates high probability of detection with false alarms significantly below 1%. Static fields of 0.2 to 0.3 Tesla are typical for permanent magnet arrays.

Figure 1B:
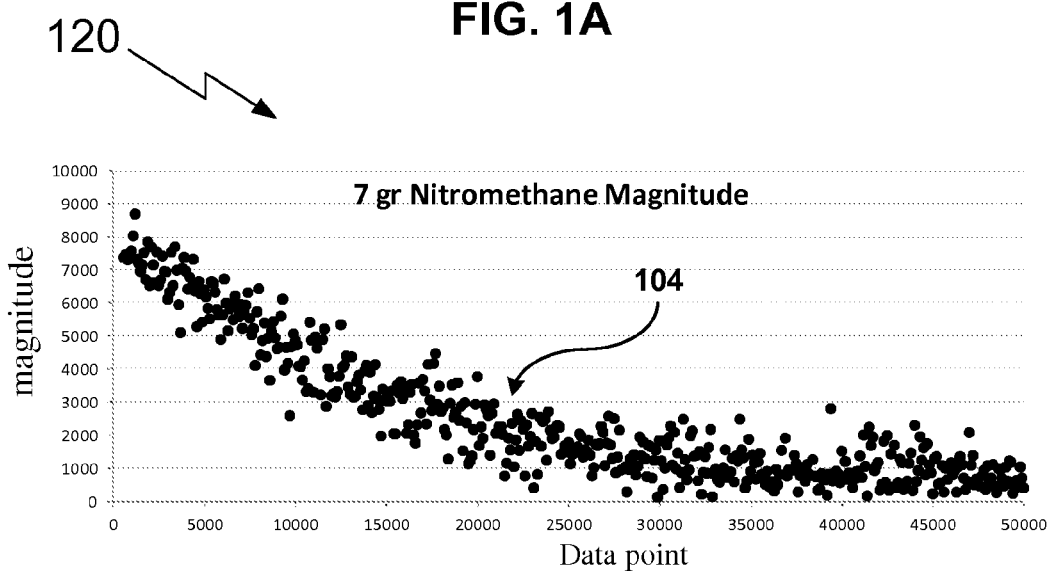
FIG. 1B shows a graph of a time series of nitromethane $^{14}$N NMR signal decay with rapid accumulation of 32 scans using a CPMG pulse sequence.

FIG. 1B shows a graph 120 of the time series 122 of $^{14}N$ NMR of nitromethane with a filling factor lower than 40%. A similar sensitivity to that of nitric acid detection is achieved with 32 scans in less than 0.5 sec ($T_1=15+/-5$ ms).

With the same signal enhancement process as shown for nitric acid above, nitromethane can be readily detected within a compact probe in 1 second with filling factors of less than 40%. At lower field strengths, the sensitivity may be further increased using steady-state pulse sequences, which are effective due to the short $T_1$ of the liquids of interest.

Figure 2:
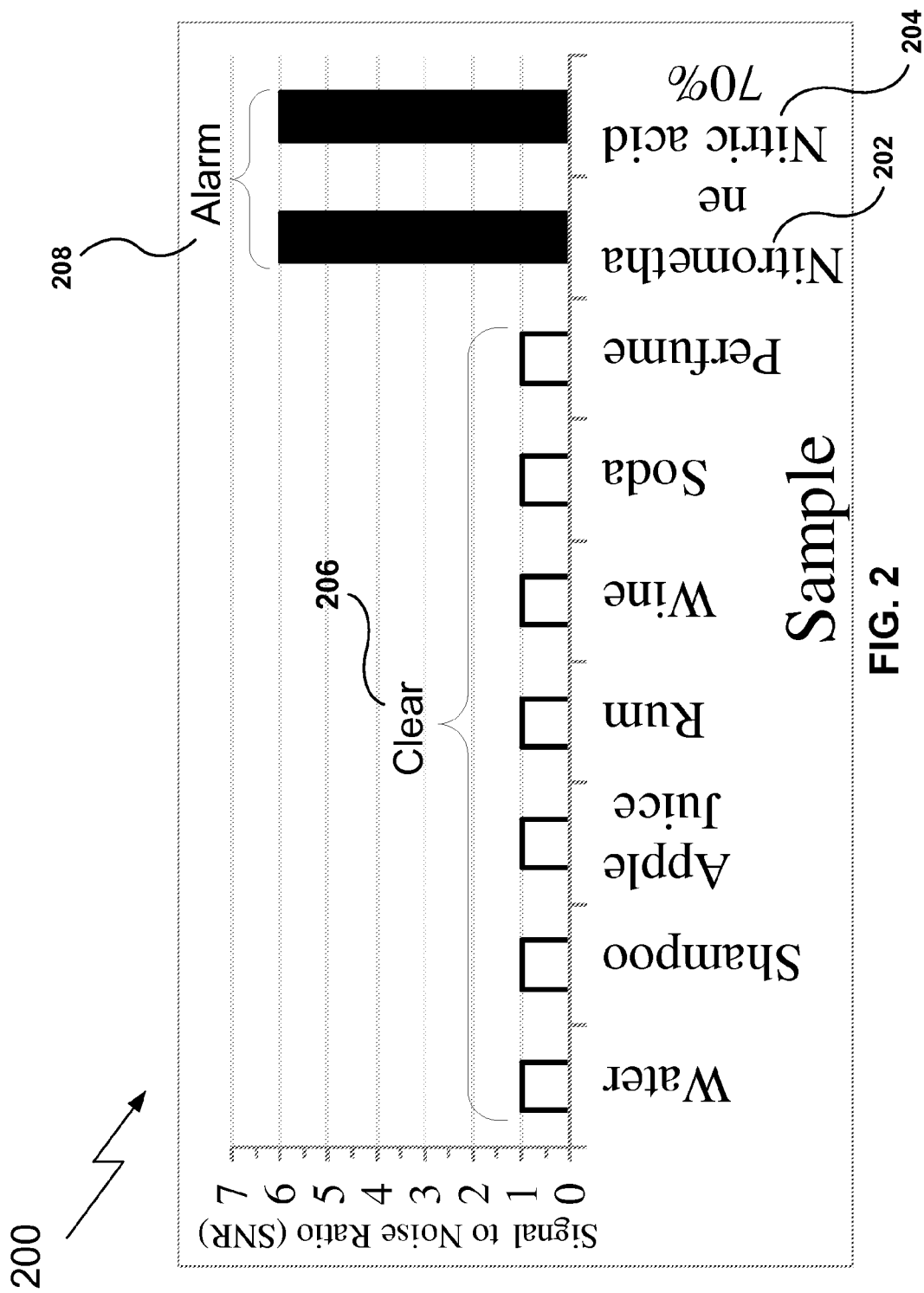
FIG. 2 shows a bar graph illustrating improved detection sensitivity of a bottle scanner based on the time series graphs of FIGS. 1A and 1B.

FIG. 2 shows the detection sensitivity for the bottle scanner based on the results with nitromethane 202 and nitric acid 204 shown above. The SNR was estimated at a lower magnetic field (0.25 Tesla) than that of the test (2.4 Tesla). A clear statistical differentiation between a Clear 206 or Alarm 208 declaration is achieved. The SNR was computed as the ratio between the signal amplitude and the noise level in the absence of nitrogen nuclei.

Peroxide-Containing Liquids

Hydrogen-containing hazardous liquids such as explosive precursors (e.g., hydrogen peroxides and peroxide mixtures) are identified by NMR by way of their distinctive NMR responses. Identifying hydrogen containing liquids may be done using certain parameters, and without the need to have any information about the liquids to be scanned prior to the inspection. Parameters used to identify hydrogen-containing explosive precursor liquids may include a combination of at least two of the following:

A. Spin-spin relaxation times ($T_2$), or signal decay times ($T_{2eff}$) during a CPMG-type pulse sequence;
B. Spin-lattice relaxation times ($T_1$); and
C. Diffusion constant.

Spin-spin relaxation is the mechanism by which the transverse component of the magnetization vector exponentially decays towards its equilibrium value of zero in NMR. Also known as the spin-spin relaxation time, or $T_2$, $T_2$ is a time constant characterizing the signal decay. It is named in contrast to $T_1$, the spin-lattice relaxation time. Spin-lattice relaxation is the mechanism by which an excited magnetization vector comes into thermodynamic equilibrium with its surroundings (the "lattice") in NMR. All of the above parameters may be rapidly measured in, for example, a one second time scale.

Figure 3:
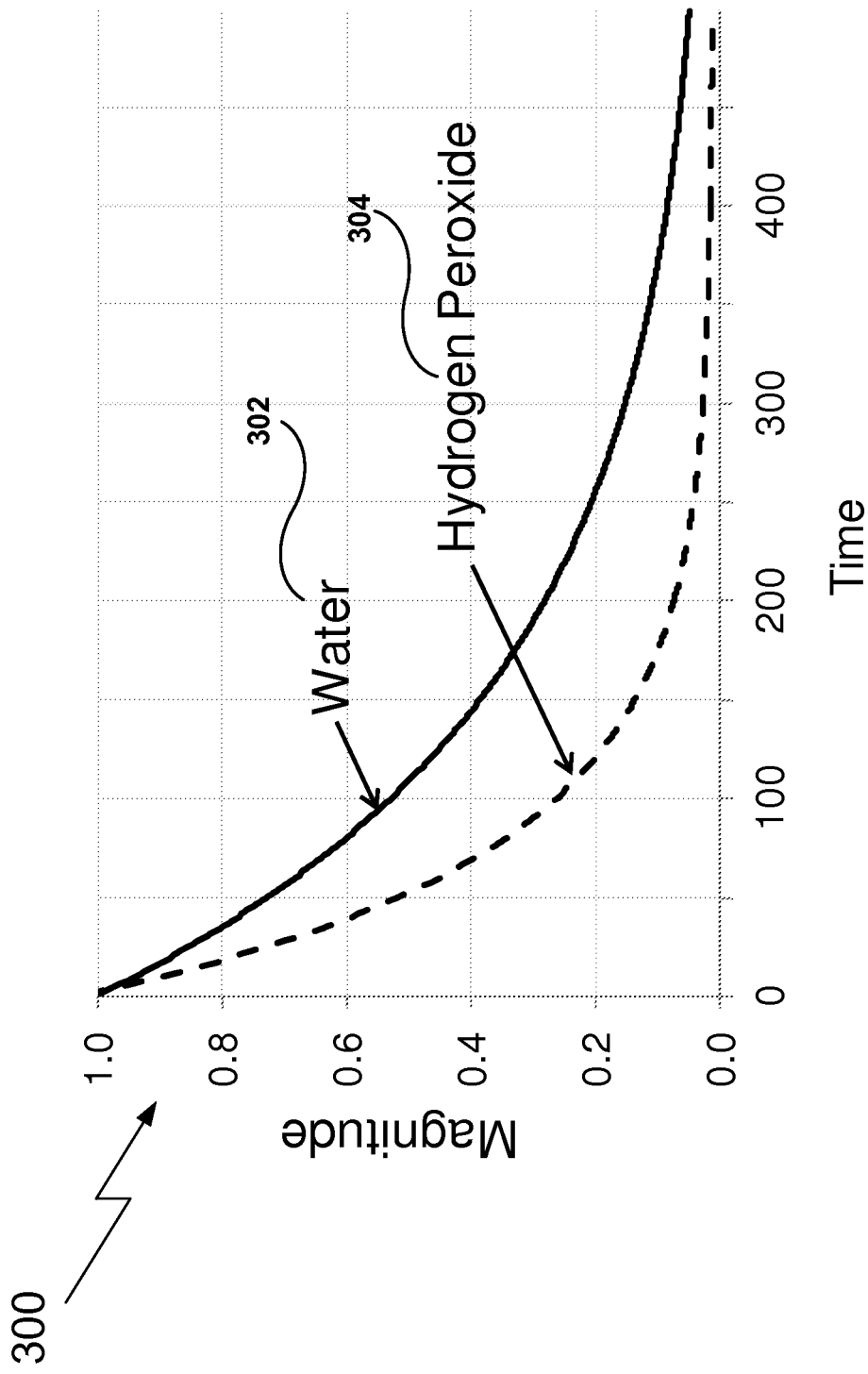
FIG. 3 shows a graph illustrating a comparison of the measured signal decay times ($T_{2eff}$) of low-concentration hydrogen peroxide ($H_2O_2$) and water.
Figure 4:
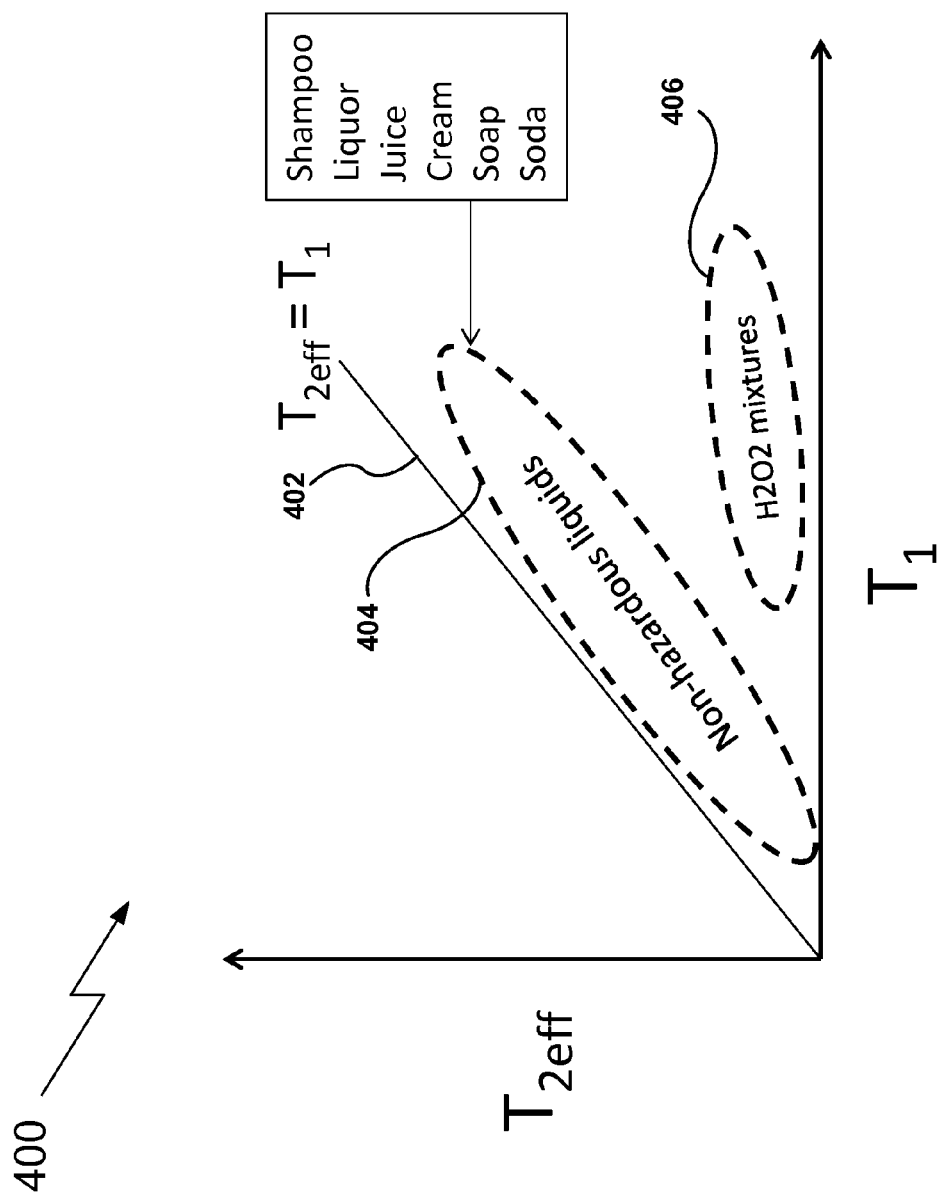
FIG. 4 shows a graph illustrating areas of the effective signal decay times ($T_{2eff}$) vs. spin-lattice ($T_1$) measurements for non-hazardous liquids and for hydrogen peroxide ($H_2O_2$) mixtures.

Hydrogen peroxide has a significantly lower spin-spin relaxation time than that of water, as shown by a comparison of plot line 302 and plot line 304 of FIG. 3. However, the spin-spin relaxation time of hydrogen peroxide is comparable to that of some cosmetic creams. Hence, the comparison of the ratios of distinctively short $T_2$ and long $T_1$ parameters enables hydrogen peroxide liquids or mixtures to be distinguished from non-hazardous liquids such a cosmetic creams as illustrated in FIG. 4.

Another parameter that may be used is the signal decay time, $T_{2eff}$, also known as the effective transverse relaxation time. Graph 400 of FIG. 4 shows areas of the $T_{2eff}$ vs. $T_1$ measurements for non-hazardous liquids distinctively separated from their counterparts for hydrogen peroxide ($H_2O_2$) mixtures. In FIG. 4, line 402 represents a plot line where $T_{2eff}=T_1$, area 404 of the graph represents that portion of graph of $T_{2eff}$ vs. $T_1$ measurements that encompasses non-hazardous liquids, and area 406 of the graph represents that portion of graph that encompasses $H_2O_2$ mixtures.

In a perfectly homogeneous magnetic field $T_{2eff}=T_2$, but $T_{2eff}$ has a shorter echo time when the field is inhomogeneous. $T_{2eff}$ for hydrogen peroxide varies in a distinctive manner as the inter echo time (TE) is changed. FIGS. 5A 500 and 5B 510 show $T_{2eff}$ for a CPMG pulse sequence with varying time echo times for pharmacy grade hydrogen peroxide (3%) 504 and water 506, respectively.

Figure 6A:
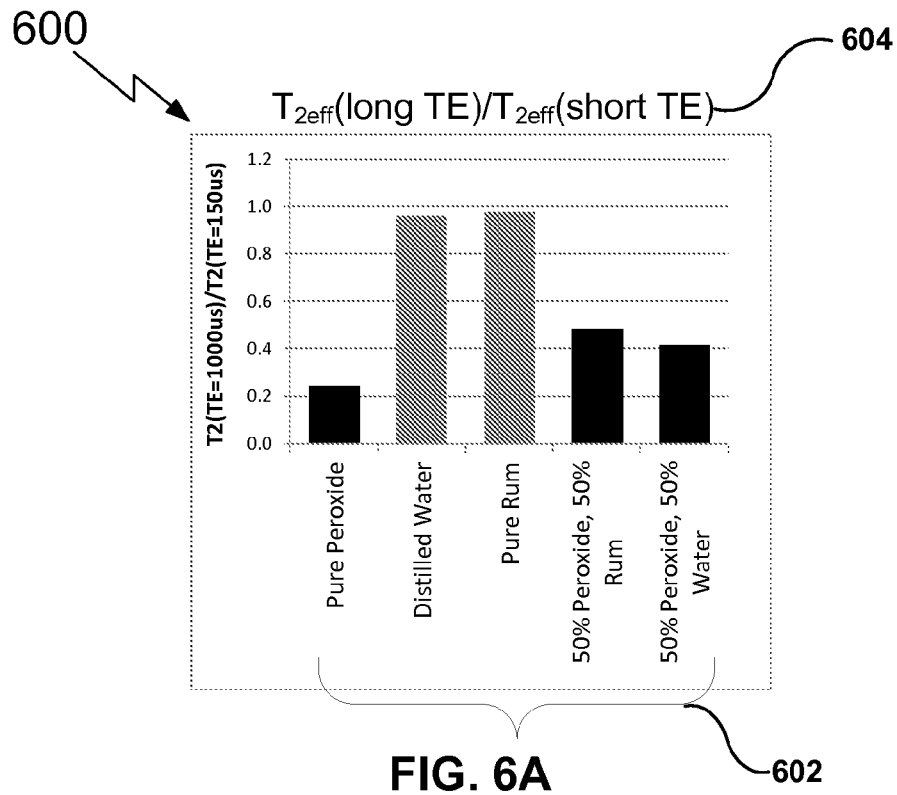
FIG. 6A shows a bar chart of the ratios of $T_{2eff}$ at two inter-echo times for pure peroxide, distilled water, pure rum, 50% low-concentration peroxide and 50% rum, and 50% peroxide and 50% water.
Figure 6B:
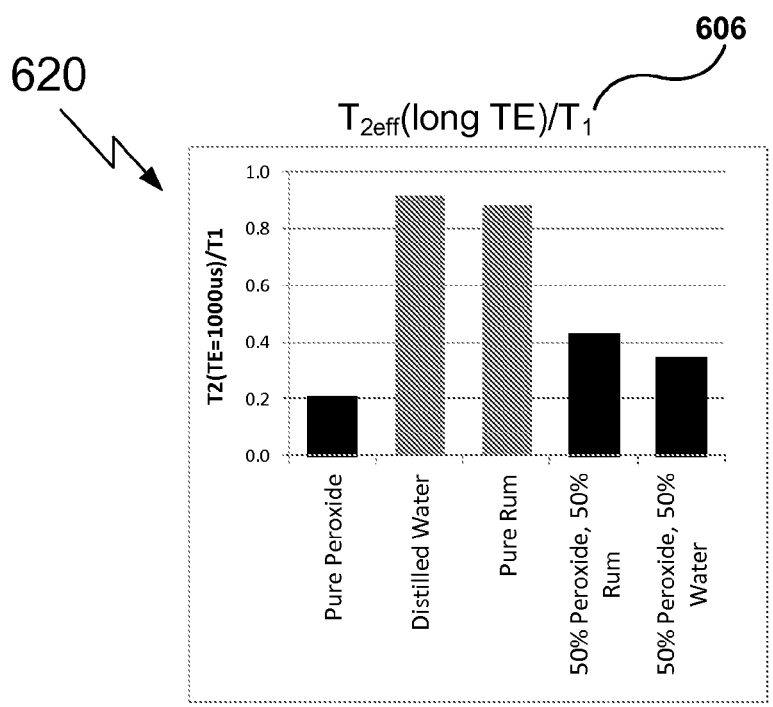
FIG. 6B shows a bar chart of the ratios of $T_{2eff}$ and $T_1$ for low-concentration peroxide, distilled water, pure rum, 50% peroxide and 50% rum, and 50% low-concentration hydrogen peroxide and 50% water.
Figure 6C:
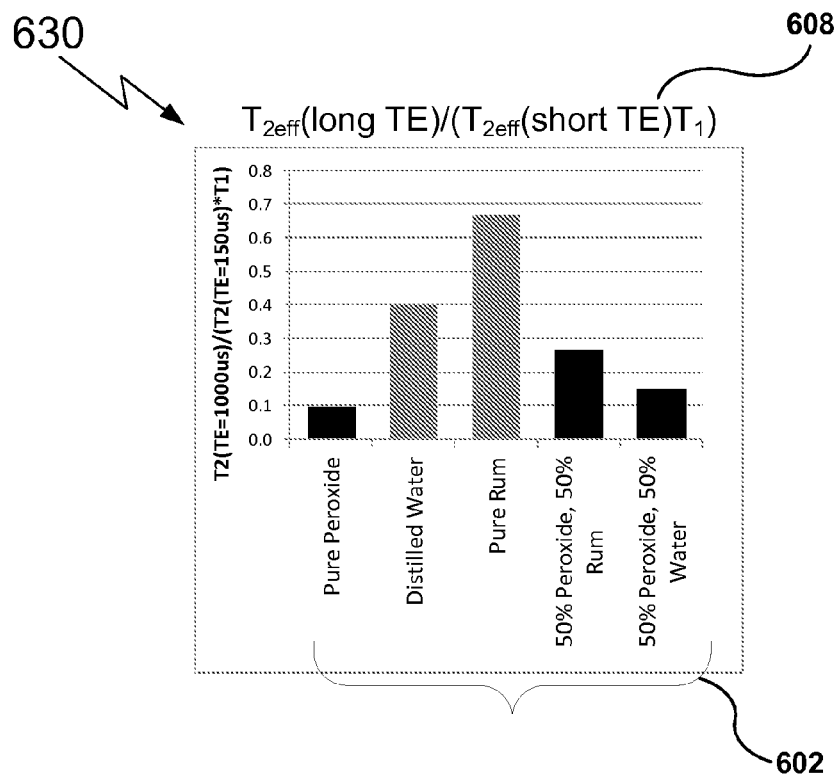
FIG. 6C shows a bar chart of the ratios of $T_{2eff}$ with a long TE to the product of $T_{2eff}$ with a short TE and $T_1$ for pure peroxide, distilled water, pure rum, 50% peroxide and 50% rum, and 50% low-concentration peroxide and 50% water.
Figure 6D:
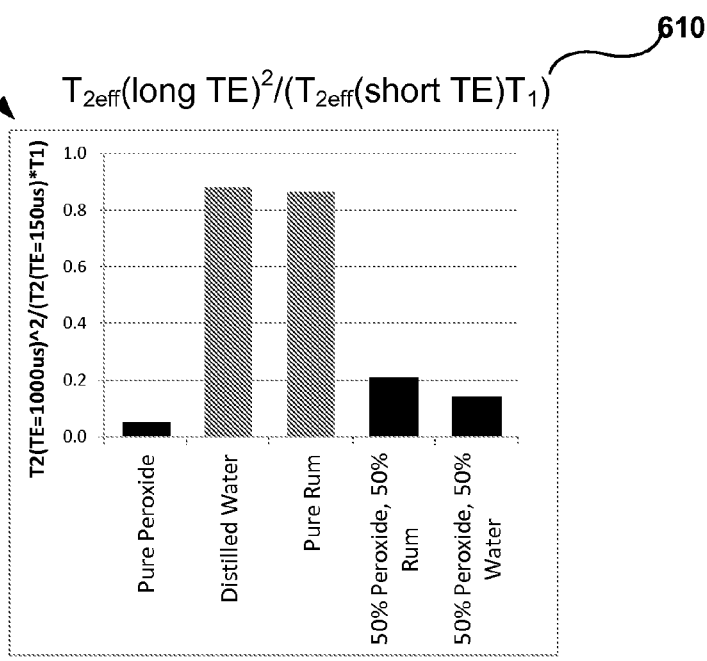
FIG. 6D shows a bar chart of the ratios of the square of $T_{2eff}$ with a long TE to the product of $T_{2eff}$ with a short TE and $T_1$ for pure peroxide, distilled water, pure rum, 50% low-concentration peroxide and 50% rum, and 50% low-concentration peroxide and 50% water.

Further, effective detection of hydrogen peroxide using various discriminators from a hydrogen NMR measurement is illustrated by FIGS. 6A-6D. All four cases include measurements for hydrogen peroxide, distilled water, pure rum, 50% peroxide and 50% rum, and 50% peroxide and 50% water. FIG. 6A 610 shows the ratio of $T_{2eff}$ at two inter-echo times. FIG. 6B 620 shows the ratio of $T_{2eff}$ and $T_1$. FIG. 6C 630 shows the ratio of $T_{2eff}$ divided by $T_1$. Finally, FIG. 6D 640 shows the ratio of $T_{2eff}$ times $T_{2eff}$ at long inter-echo times, divided by $T_1$.

The diffusion coefficient or diffusion constant (D) is yet another effective parameter to characterize liquids. The diffusion coefficient is calculated using Equation (1) below.

$$(1/T_{2eff}) = 1/T_2 + (1/3)\gamma^2 G^2 D T E^2, \quad (1)$$

which may be defined as $$1/T_{2eff} = 1/T_2 + 1/T_{2G}; \text{ with } T_{2G} = 3/(\gamma^2 G^2 D T E^2). \quad (2)$$

The inhomogeneous field contribution ($1/T_{2G}$) is determined by the static magnetic field gradient (G), the diffusion coefficient of the inspected liquid (D), and the gyromagnetic ratio ($\gamma/2\pi = 4.3$ kHz/G for protons), where $T_E$ is the inter-echo duration. Therefore $$D = 3/(\gamma^2 G^2)(1/T_{2effA} - 1/T_{2effB})/(TE_A^2 - TE_B^2);$$

where the subscripts A and B indicate the two measurements with different echo times.

The selection of any two of the above parameters is performed with the goal of optimizing the detection of hydrogen in the samples during the screening process. A hydrogen-containing hazardous liquid is detected by evaluating their responses in the multi-dimensional NMR parameter space, such as the $T_{2eff}$ v. $T_1$ two dimensional space example shown in FIG. 4.

Examples of Detection Schemes

Samples may be placed directly on an open probing head or in an enclosed magnet. Enclosed magnets may be comprised of a conventional dipole magnet or a Halbach array generating effectively uniform magnetic fields. The NMR scanning clears the inspected samples only after scans foscans for hydrogen-containing and nitrogen-containing liquids have been completed and both have provided negative responses. A positive response in either step results in an alarm declaration. The alarm declaration may be triggered as soon as either of the scans detects a hazardous liquid, without the need to complete the scan. FIG. 11, described below, is generally schematically representative of an NMR apparatus or system that may be utilized for implementing the detection methods described herein.

Figure 7:
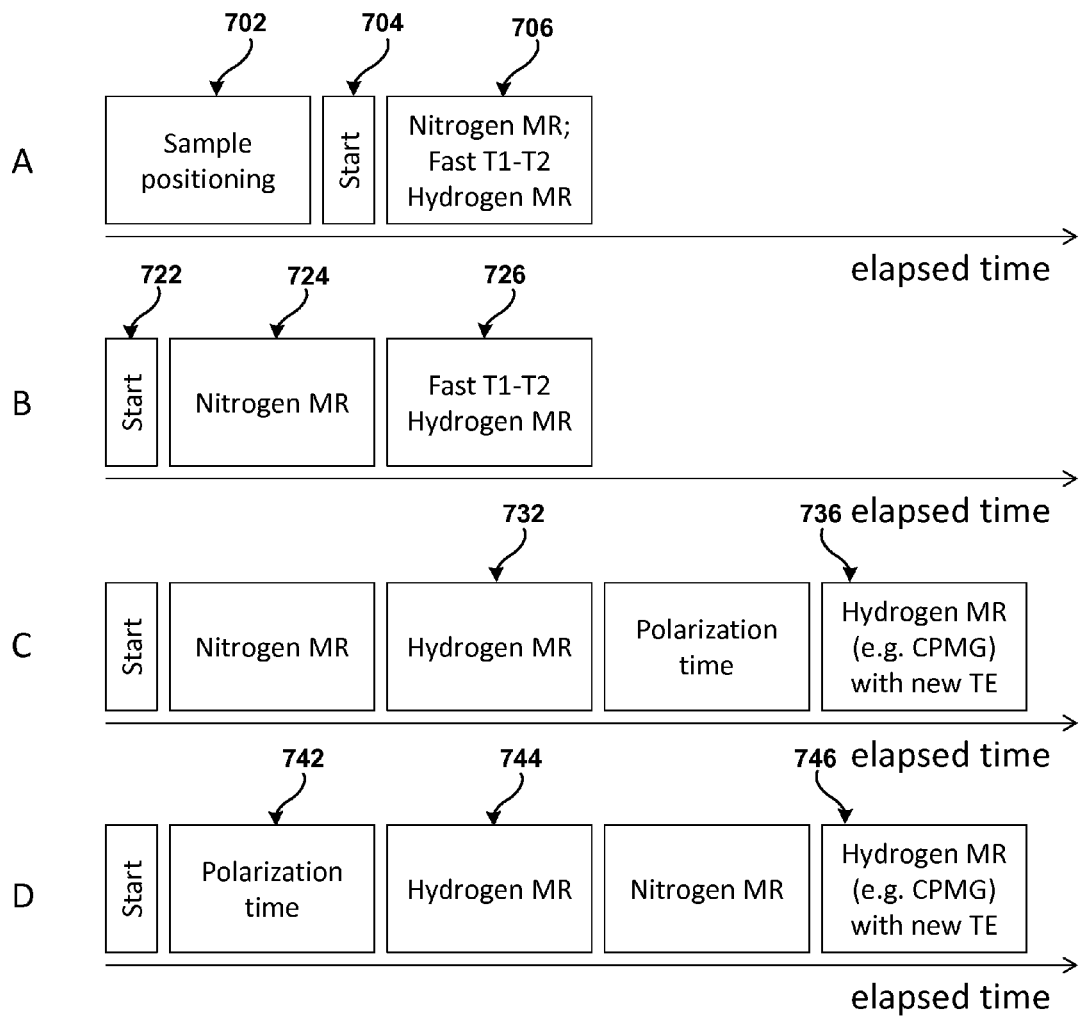
FIG. 7 shows a block diagram outlining four different detection schemes that may be used to detect hydrogen and nitrogen in a given liquid.

The operational advantages of the proposed detection schemes include a fast, high-performance alternative to existing hazardous liquid detection methods. NMR detection schemes disclosed herein combine hydrogen and nitrogen measurements. Hydrogen and nitrogen measurements may be performed simultaneously or sequentially. FIG. 7 schematically shows the timing sequences of four examples of detection schemes. Other detection schemes may be used, and the sequence of detection processes may change based on the targets of interest and the capabilities of the instruments. Prior to commencing an NMR pulse sequence, the spin system needs to achieve a measurable level of polarization, dictated by the spin-lattice or polarization time $T_1$. $T_1$ for the nitrogen response is typically milliseconds to tens of milliseconds, while for hydrogen-based measurements, $T_1$ may be as long as a few seconds.

Detection scheme A, as shown in FIG. 7, is the fastest detection scheme of the four schemes of FIG. 7. In block 706, the measurements and testing of hydrogen and nitrogen are conducted simultaneously. The data acquisition and gathering commences after an elapsed time that allows for spin system polarization. The polarization time may be determined by triggering a timer as the sample is positioned in block 702. The data acquisition may then be triggered at a predetermined elapsed time in block 704. This ensures sufficient polarization time prior to data acquisition. $T_1$ and $T_2$ measurements follow in block 706, using a fast protocol. For example, a fast $T_1$ measurement may involve the use of short RF pulses to dynamically evaluate polarization growth, without significantly saturating the sample. An echo train sequence, such as CPMG, follows to compute $T_2$ or $T_{2eff}$. These parameters are used to detect all nitrogen-containing liquids, hydrogen peroxide and hydrogen peroxide mixtures.

Fast $T_1$-$T_2$ Computation is one example of fast protocols utilized to conduct $T_1$ and $T_2$ measurements. A $T_1$ measurement may be triggered immediately after the bottle is placed in the instrument. A sequence of short RF pulses is used and the Free Induction Decay (FID) signals following the pulses are measured. The pulse duration $t_p \ll t_{180}$, where $t_{180}$ is the duration of the RF pulse to produce a full inversion of the spin magnetization.

The polarization (A) increases exponentially, following:

$$A = A_0[1 - \exp(-t/T_1)],$$

where $A_0$ is full polarization level, and t is the elapsed time from bottle placement (or after a set of magnetization spoiling pulses) to the RF pulse transmission. The exponential time constant $T_1$ is then computed by a least square fit to the signal amplitude at two or more times.

After the $T_1$ measurement protocol is completed, a CPMG measurement is performed to compute $T_{2eff}$. An option to measure relaxation times and diffusion constants is to run two CPMG measurements, using different time between echoes, TE. Diffusion constants are computed using the $T_{2eff}$ from both sequences. The $T_1$ parameter is computed using the signal amplitudes. For example, if the first scan is performed after the spin system is effectively polarized, $A_0$ is measured directly with the first scan. Following the exponential increase shown above, the relaxation time $T_1$ may be computed by;

$$T_1 = t_1 / \ln [1/(1 - A_1/A_0)],$$

where $A_1$ and $t_1$ are the signal amplitude and polarization time for the second scan.

In order to ensure that the CPMG measurement yields a signal amplitude that is independent of the time between echoes, the amplitude may be computed by a square fit of the exponential decay during the echo train and extrapolating to the initial time of the scan:

$$A_1 = A_0 \exp(t_1 / T_{2eff}),$$

where $A_1$ is the echo amplitude at time $t_1$.

The computed NMR parameters are compared to those of the hazardous material, as shown in FIG. 4, for a two-dimensional $T_1$ and $T_2$ analysis to screen for explosive precursors, such as hydrogen peroxide and hydrogen peroxide mixtures.

Detection scheme B, as shown in FIG. 7, follows the same process described in detection scheme A above, with the exception that the hydrogen and nitrogen measurements are conducted sequentially in blocks 724 and 726, respectively. Therefore, the hydrogen polarization time occurs during the nitrogen NMR measurement (block 724).

Similarly, detection scheme C, as shown in FIG. 7, features the sequential measurements of hydrogen and nitrogen, where the hydrogen measurement has two components, blocks 732 and 736. In block 732, an initial scan may be conducted to measure $T_2$ or $T_{2\mathit{eff}}$ using, for example, a CPMG sequence. A second scan may be conducted in block 736 using a different time between echoes (TE), allowing the computation of the diffusion constant and $T_1$, as explained above with reference to FIGS. 6A-6D.

Detection scheme D, as shown in FIG. 7, is similar to detection scheme C, with the exception that detection scheme D commences with a hydrogen polarization period in block 742. If a hydrogen NMR scan is performed initially (in block 744) and a second one is performed after the nitrogen scan (in block 746), the $T_1$ time may be computed comparing the signal level of the two scans and using an exponential decay model.

Figure 8:
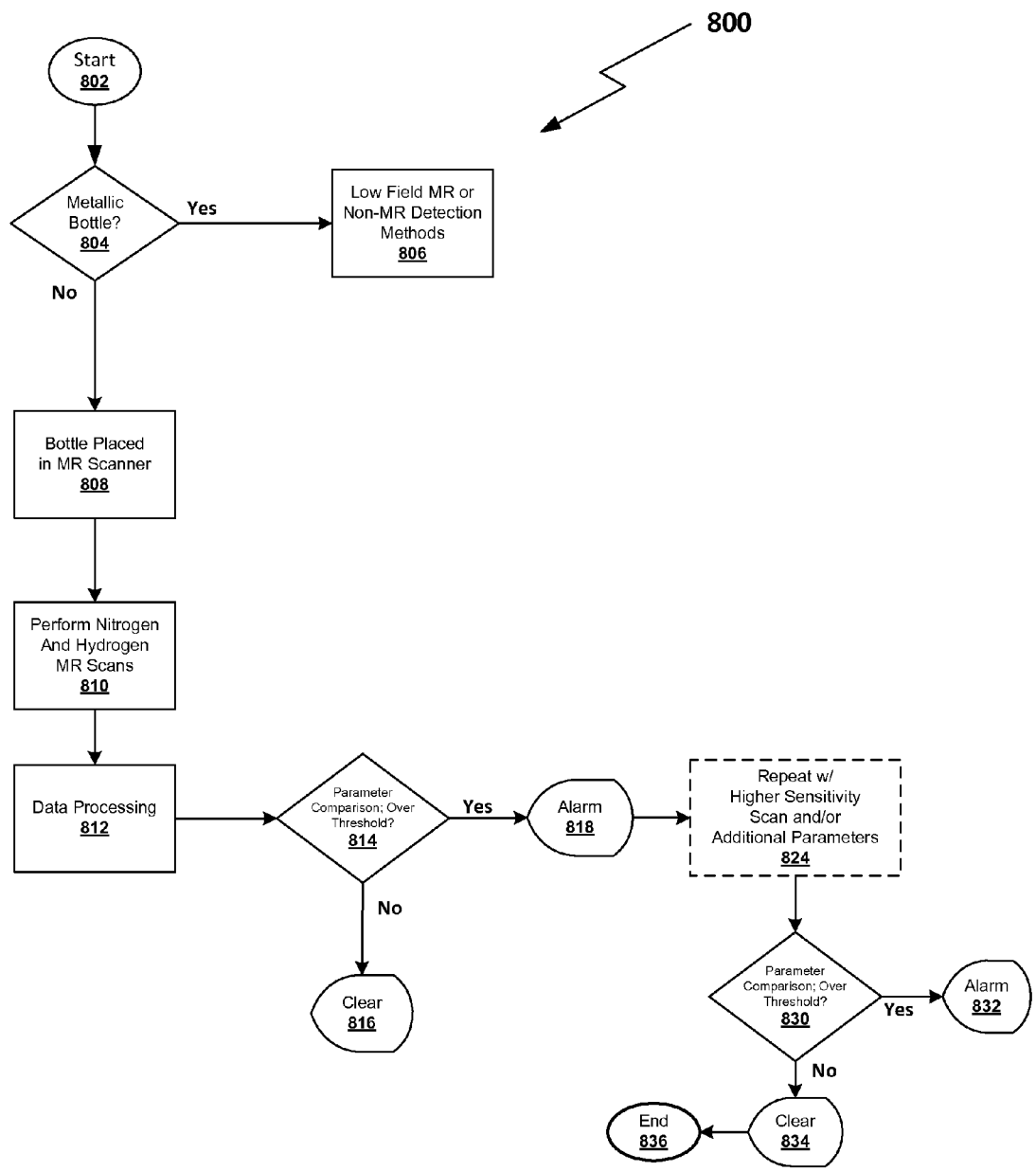
FIG. 8 shows a flow chart of an example of a method of a type of detection scheme A shown in FIG. 7, where the Alarm or Clear declaration is performed after the nitrogen and hydrogen scans are complete.

Turning to FIG. 8, a flow diagram 800 of the steps for detecting peroxides and nitrogen in an unopened container in accordance with one example of an implementation of the invention is shown. The detection scheme shown in FIG. 8 corresponds to detection scheme A of FIG. 7, or to any method that completes the data collection and data processing for both nitrogen and hydrogen prior to providing an Alarm or Clear declaration. The process starts at step 802, and in decision step 804, the process begins by determining if the container to be examined is metallic, in which case the container will have to be screened with other methods, such as a low-field MR scanning method or a non-NMR method, e.g., weighing metallic cans to identify liquid alteration.

In step 808, the container is placed in an MR scanner, and in step 810, $^{14}N$ NMR and $^{1}H$ proton NMR scans are performed simultaneously. In step 812, data processing takes place, which may comprise calculating ratios of $T_1$ and $T_2$ times, of $T_{2\mathit{eff}}$ times with different TE times, of $T_{2\mathit{eff}}$ and $T_1$ times, and various combinations thereof.

In decision step 814, the ratios and other parameters are compared to predetermined thresholds, and if all ratios and parameters are below the corresponding thresholds, then the Clear declaration is displayed in step 816. If a ratio or parameter exceeds a threshold, the process then proceeds to optional step 824 where the $^{14}N$ NMR and $^{1}H$ proton NMR scans may be repeated using higher sensitivity scans and/or measuring additional parameters. In decision step 830, the re-calculated ratios and other parameters are compared to another set of predetermined thresholds, and if all ratios and parameters are below the corresponding thresholds, then the Clear declaration is displayed in step 834 and the process ends in step 836. If a ratio or parameter exceeds a threshold, the process then proceeds to step 832 where the Alarm declaration is displayed and the process ends in step 840.

Figure 9:
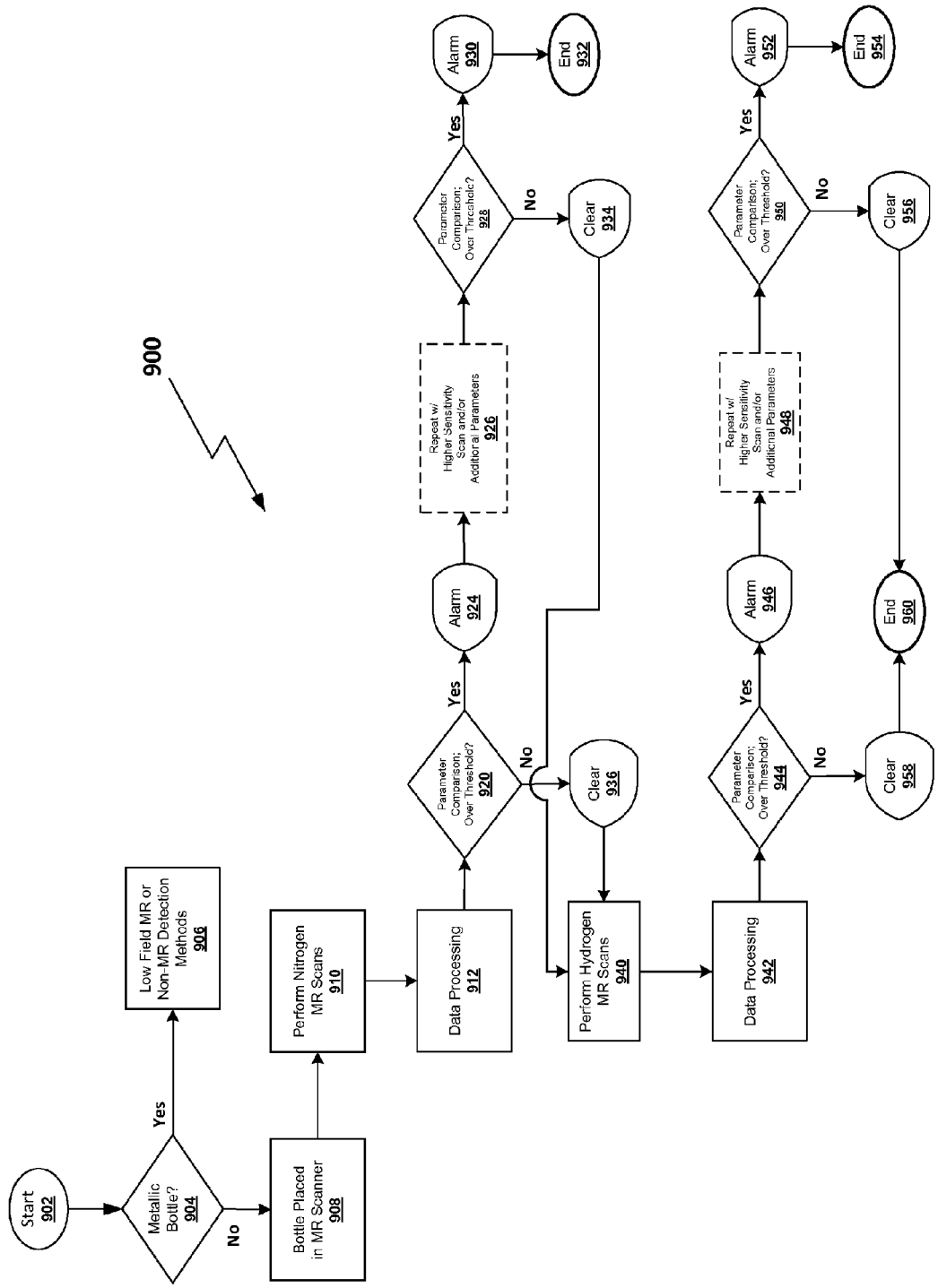
FIG. 9 shows a flow chart of an example of a method of a type of detection schemes B or C shown in FIG. 7, where the NMR parameters for the specific material detection is performed after the nitrogen detection step.

In FIG. 9, a flow diagram 900 of the steps for detecting peroxides and nitrogen in an unopened container in accordance with another example of an implementation of the invention is shown. The detection scheme shown in FIG. 9 corresponds to detection schemes B and C of FIG. 7 in that the data collection and data processing for nitrogen and hydrogen are performed sequentially, where an Alarm or Clear declaration may be displayed in each stage. Step 902, decision step 904, and step 908 are similar to step 802, decision step 804, and step 808, respectively, of FIG. 8.

In step 910, $^{14}N$ NMR scans are performed, and in step 912, data processing takes place, which may comprise sensitivity-enhanced scans using CPMG pulse sequences as described in relation to FIGS. 1A and 1B. In decision step 920, the ratios and other parameters are compared to predetermined thresholds, and if all ratios and parameters are below the corresponding thresholds, then the Clear declaration is displayed in step 936 and the process proceeds to step 940.

If a ratio or parameter exceeds a threshold, an Alarm declaration is displayed in step 924 and the process proceeds to optional step 926 where the $^{14}N$ NMR scans may be repeated using higher sensitivity scans and/or measuring additional parameters. In decision step 928, the re-calculated ratios and other parameters are compared to another set of predetermined thresholds, and if all ratios and parameters are below the corresponding thresholds, then the Clear declaration is displayed in step 934 and the process proceeds to step 940. If a ratio or parameter exceeds a threshold, the process then proceeds to step 930 where the Alarm declaration is displayed and the process ends in step 932.

In step 940, $^{1}H$ proton NMR scans are performed and in step 942, data processing takes place, which may comprise calculating ratios of $T_1$ and $T_2$ times, of $T_{2\mathit{eff}}$ times with different TE times, of $T_{2\mathit{eff}}$ and $T_1$ times, and various combinations thereof. In decision step 944, the ratios and other parameters are compared to predetermined thresholds, and if all ratios and parameters are below the corresponding thresholds, then the Clear declaration is displayed in step 958 and the process ends in step 960.

If a ratio or parameter exceeds a threshold, an Alarm declaration is displayed in step 946 and the process then proceeds to optional step 948 where the $^{1}H$ proton NMR scans may be repeated using higher sensitivity scans and/or measuring additional parameters. In decision step 950, the re-calculated ratios and other parameters are compared to another set of predetermined thresholds, and if all ratios and parameters are below the corresponding thresholds, then the Clear declaration is displayed in step 956 and the process ends in step 960. If a ratio or parameter exceeds a threshold, the process then proceeds to step 952 where an Alarm declaration is displayed and the process ends in step 954

Figure 10:
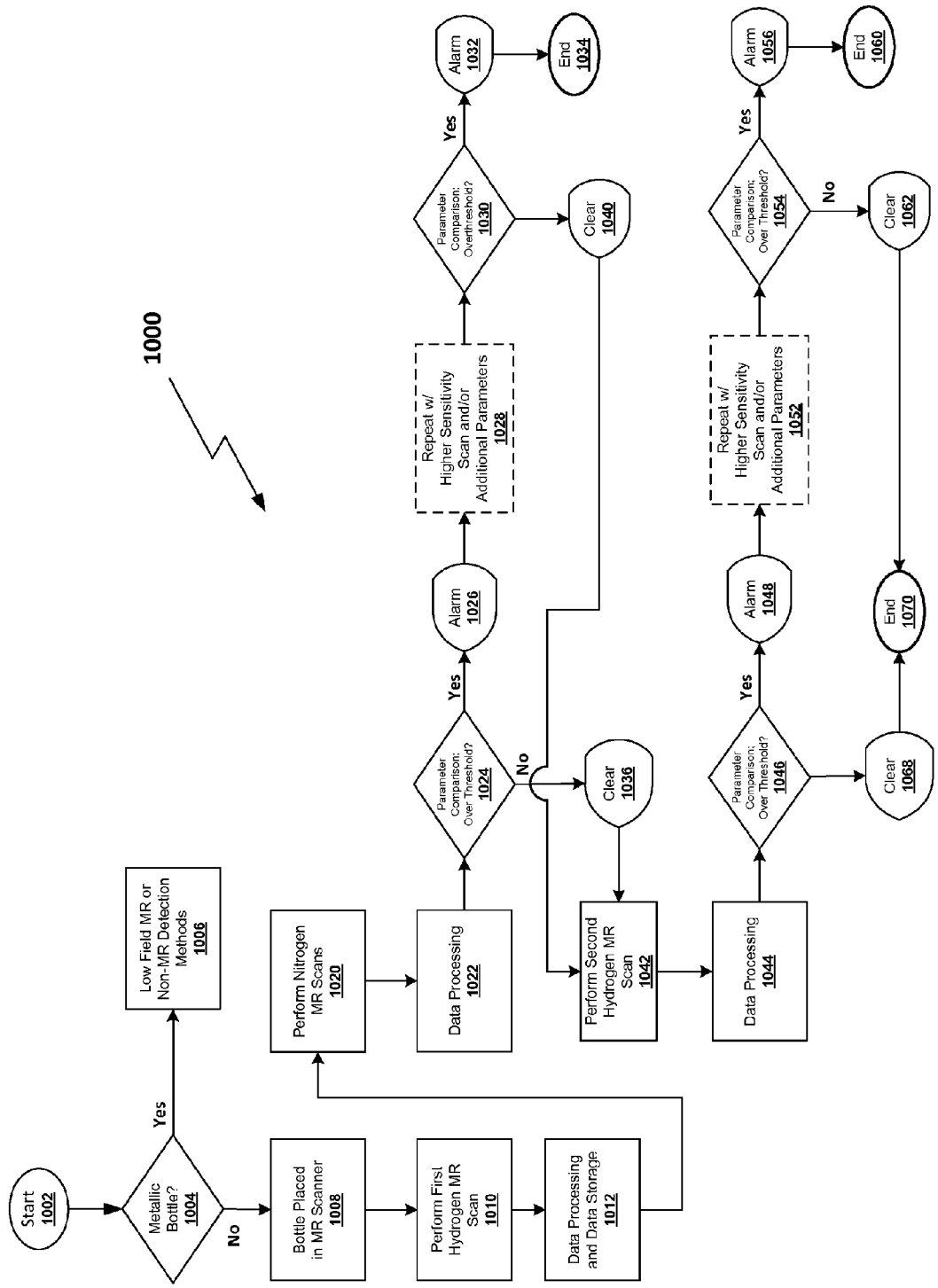
FIG. 10 shows a flow chart of an example of a method of a type of detection scheme D shown in FIG. 7, where the hydrogen NMR measurements for the specific material detection are performed in two stages: a) an initial scan and b) a final scan after the nitrogen detection step.

In FIG. 10, a flow diagram 1000 of the steps for detecting peroxides and nitrogen in an unopened container in accordance with yet another example of an implementation of the invention is shown. The detection scheme shown in FIG. 10 corresponds to detection scheme D of FIG. 7 in that the data collection and data processing for hydrogen comprises two components, a first scan and a second scan. The first component comprises steps 1010 and 1012, which may be used to measure $T_2$ and $T_{2\mathit{eff}}$ times using, for example, a CPMG sequence. This may be followed by an $^{14}N$ NMR scan comprising steps 1020-1036, which are similar to the corresponding steps in FIGS. 8 and 9.

In steps 1042 and 1044, the data collection and data processing of the second component are performed are performed, which may comprise using a different time between echoes (TE), thus allowing a calculation of a diffusion constant (D) and $T_1$ as more fully described above with respect to FIGS. 6A-6D. Following step 1044, the ratios and other parameters are compared to predetermined thresholds in decision step 1046, and if all ratios and parameters are below the corresponding thresholds, then the Clear declaration is displayed in step 1068 and the process ends in step 1070.

If a ratio or parameter exceeds a threshold, an Alarm declaration is displayed in step 1048 and the process proceeds to optional step 1052 where the second stage $^{1}H$ proton NMR scans may be repeated using higher sensitivity scans and/or measuring additional parameters. In decision step 1054, the re-calculated ratios and other parameters are compared to another set of predetermined thresholds, and if all ratios and parameters are below the corresponding thresholds, then the Clear declaration is displayed in step 1062 and the process ends at step 1070. If a ratio or parameter exceeds a threshold, the process then proceeds to step 1056 where the Alarm declaration is displayed and the process ends at step 1060.

FIG. 11 shows a schematic block diagram of an apparatus 1100 configured to perform methods of receiving and scanning unopened non-metallic containers to detect hazardous materials using NMR technology. The apparatus 1100 comprises a magnet 1120, which may be an enclosed magnet such as a conventional dipole magnet or a Halbach array generating effectively uniform magnetic fields. Bottle or container 1124 is any non-metallic container holding the liquid to be examined.

In a method operation, the container 1130 is placed in the apparatus 1100 such that the container 1130 is positioned within a magnetic field generated by the magnet 1120. The Nitrogen-Hydrogen RF Controller 1106 then excites the container 1130 with electromagnetic pulses having a frequency corresponding to $^{1}H$ NMR and N NMR, where the electromagnetic pulses are transmitted to the Transmitter-Power Amplifier 1108 and then to the RF Switch 1114. The appropriate frequency responses may be set by a user through the User Interface—Alarm/Clear 1102 module, which may include a display and Graphical User Interface (GUI).

Signals are then received through a radio frequency (RF) probe 1124, which may be a dual-tuned radio-frequency probe that switches the resonance frequency of a single coil or antenna, or a pair of physically separated nitrogen and hydrogen coils or antennas. The FID signals are amplified in Signal Amplifier 1110 and in the Data Processing PC/Controller 1104, the amplified signals are evaluated by detecting and evaluating NMR signal amplitudes and relaxation times as described above. In this example, the Data Processing PC/Controller 1104 may be a controller device, microcontroller, processor, microprocessor, application specific integrated circuit ("ASIC"), digital signal processor ("DSP"), or other similar device. As described in FIGS. 8-10, various parameters are determined and compared with predetermined thresholds and based on this comparison, Alarm and Clear declarations may be displayed to the user through the User Interface—Alarm/Clear 1102 module. These declarations may be audio signals, such as tones, bells, and spoken words, visual signals, such as flashing lights, and text or icons displayed on a monitor, and any other type of signal that will convey the results of the comparisons to the user. The user may input parameters and other inputs to the apparatus 1100; however, the liquid in the container 1130 may also be inspected by automated protocols such that an Alarm or Clear declaration is provided to the user without the need for little, if any, operator interpretation.

The foregoing description of implementations has been presented for purposes of illustration and description. It is not exhaustive and does not limit the claimed inventions to the precise form disclosed. Modifications and variations are possible in light of the above description or may be acquired from practicing examples of the invention. The claims and their equivalents define the scope of the invention.

What is claimed is:

1. A method for detecting hazardous materials, the method comprising:
   positioning a non-metallic container holding a liquid sample in a static magnetic field;
   applying a first nuclear magnetic resonance (NMR) pulse sequence to the liquid sample having a frequency corresponding to a proton NMR frequency in the static magnetic field;
   receiving a first plurality of NMR measurement signals from the liquid sample responsive to the proton NMR frequency;
   measuring relaxation times of the plurality of NMR measurement signals received, wherein said measuring comprises measuring spin-lattice relaxation times ($T_1$ and effective multi-pulse sequence signal decay time ($T_{2eff}$) and measuring $T_{2eff}$ times having different echo times (TE);
   applying a second NMR pulse sequence to the liquid sample having a frequency corresponding to a $^{14}N$ NMR frequency in the static magnetic field;
   receiving a second plurality of NMR measurement signals from the liquid sample responsive to the $^{14}N$ or the proton NMR frequency;
   measuring signal amplitudes of the second plurality of NMR measurement signals;
   calculating ratios of the $T_1$ times and the $T_{2eff}$ times;
   comparing each of the ratios determined from the first plurality of NMR measurement signals received to corresponding predetermined thresholds;
   generating an alarm indication if any of the ratios exceeds the corresponding predetermined threshold that indicates the presence of explosive precursors in the liquid sample;
   after generating the alarm indication, applying a third NMR pulse sequence having a frequency corresponding to a proton NMR frequency to the liquid sample providing a higher sensitivity scan;
   receiving a third plurality of NMR measurement signals; and
   measuring additional relaxation times and signal amplitudes of the third plurality of NMR measurement signals received.

2. The method of claim 1, further including the steps of:
   comparing parameters determined from the first plurality of NMR measurement signals received to corresponding parameters of predetermined hazardous materials such as explosive precursors; and
   generating an alarm if any of the parameters is equal to or within a specified range of the parameters corresponding to the predetermined hazardous materials.

3. The method of claim 1, further including the steps of:
   calculating ratios of $T_{2eff}$ and $T_1$ times from the third plurality of NMR measurement signals; comparing each of the ratios determined from the third plurality of NMR measurement signals received to corresponding predetermined thresholds that indicate the presence of explosive precursors in the liquid sample; and
   generating an alarm indication to the user if the any of the ratios exceeds the corresponding predetermined threshold.

4. The method of claim 3, further including the steps of:
   comparing parameters determined from the plurality of NMR measurement signals received from the higher sensitivity scan to corresponding values of predetermined hazardous materials such as explosive precursors; and
   generating an alarm if any of the parameters is equal to or within a specified range of the parameters corresponding to the predetermined hazardous materials.

5. The method of claim 3 further including the steps of:
comparing each of the ratios determined from the second plurality of NMR measurement signals to corresponding predetermined thresholds that indicate the presence of nitrogen in the liquid sample; and
generating an alarm indication if any of the ratios exceeds the corresponding predetermined threshold.

6. The method of claim 5, further including the steps of:
after the display of the alarm indication, applying a fourth NMR pulse sequence having a frequency corresponding to a $^{14}N$ NMR frequency to the liquid sample having a higher sensitivity scan;
receiving a fourth plurality of NMR measurement signals at a $^{14}N$ or a proton frequency; and measuring additional signal amplitudes of the fourth plurality of NMR measurement signals.

7. The method of claim 6, further including the steps of:
comparing the ratios determined from the fourth plurality of NMR measurement signals to predetermined thresholds that indicate the presence of nitrogen in the liquid sample; and
displaying an alarm indication if any of the ratios exceed the corresponding predetermined threshold.

8. The method of claim 1, wherein the step of measuring the signal amplitudes of the second plurality of NMR measurement signals further comprises:
using echo-train and steady-state pulse sequences resulting in noise reduction by data accumulation;
performing signal averaging by adding free induction decay or echo signals;
repeating and adding scans;
applying noise filters to the signal amplitude; and
any combination of the foregoing.

9. The method of claim 8, further including nitrogen detection by means of cross polarization.

10. The method of claim 1, where the steps of applying a first NMR pulse sequence and measuring relaxation times and signal amplitudes of the first plurality of NMR measurement signals and the steps of applying a second NMR pulse sequence and measuring relaxation times and signal amplitudes of the second plurality of NMR measurement signals are performed simultaneously.

11. The method of claim 1, where the steps of applying a first NMR pulse sequence and measuring relaxation times and signal amplitudes of the first plurality of NMR measurement signals and the steps of applying a second NMR pulse sequence and measuring relaxation times and signal amplitudes of the second plurality of NMR measurement signals are performed sequentially and in any order.

12. The method of claim 11, where the steps of receiving a first plurality of NMR measurement signals responsive to the proton NMR frequency and measuring relaxation times and signal amplitudes of the first plurality of NMR measurement signals received further include:

measuring a first set of $T_{2eff}$ times using a Carr-Purcell-Meiboom-Gill (CPMG) pulse sequence having a first inter echo time (TE);

measuring a second set of $T_{2eff}$ times using the CPMG pulse sequence having a second TE; and determining $T_1$ times and a Diffusion Constant from the first and the second sets of $T_{2eff}$ times.

13. The method of claim 12, where the Diffusion Constant is determined using the measured $T_{2eff}$ at different echo times as follows:

$$D=3/(Y^2 G^2)(1/T_{2effA}-1/T_{2effB})/(TEA^2-TEB^2).$$

14. The method of claim 12, where the steps of applying an NMR pulse sequence corresponding to a proton NMR frequency and receiving a second plurality of NMR measurement signals are performed after measuring a first set of $T_{2eff}$ times using a CPMG pulse sequence having a first TE and measuring a $^{14}N$ signal amplitude.

* * * * *